US008211051B2

(12) United States Patent
Delaporte

(10) Patent No.: US 8,211,051 B2
(45) Date of Patent: Jul. 3, 2012

(54) ELECTROACTIVE POLYMER ACTUATED CEREBROSPINAL FLUID SHUNT

(76) Inventor: Stephen E. Delaporte, East Williston, NY (US)

(*) Notice: Subject to any disclaimer, the term of this patent is extended or adjusted under 35 U.S.C. 154(b) by 803 days.

(21) Appl. No.: 11/903,665

(22) Filed: Sep. 24, 2007

(65) Prior Publication Data

US 2008/0125690 A1 May 29, 2008

Related U.S. Application Data

(60) Provisional application No. 60/846,952, filed on Sep. 24, 2006.

(51) Int. Cl.
*A61M 5/00* (2006.01)
(52) U.S. Cl. .......................................................... 604/9
(58) Field of Classification Search ............... 604/8–10, 604/93.01, 94.01, 95.01, 96.01, 104, 245–247, 604/264, 500–508; 623/3.1; 128/903; 137/1, 137/383, 385
See application file for complete search history.

(56) References Cited

U.S. PATENT DOCUMENTS

| | | | |
|---|---|---|---|
| 4,560,375 A | 12/1985 | Schulte et al. | |
| 4,615,691 A | 10/1986 | Hakim et al. | |
| 4,772,257 A | 9/1988 | Hakim et al. | |
| 5,336,166 A * | 8/1994 | Sierra | 604/9 |
| 5,387,188 A | 2/1995 | Watson | |
| 6,314,317 B1 | 11/2001 | Willis | |
| 6,533,733 B1 * | 3/2003 | Ericson et al. | 600/561 |
| 6,589,198 B1 | 7/2003 | Soltanpour et al. | |
| 6,731,976 B2 | 5/2004 | Penn et al. | |
| 6,806,621 B2 | 10/2004 | Heim et al. | |
| 6,809,462 B2 * | 10/2004 | Pelrine et al. | 310/319 |
| 6,984,395 B2 | 1/2006 | Boch et al. | |
| 7,052,594 B2 * | 5/2006 | Pelrine et al. | 205/687 |
| 7,089,783 B2 | 8/2006 | Ludin et al. | |
| 7,172,551 B2 | 2/2007 | Leasure | |
| 7,261,686 B2 | 8/2007 | Couvillon, Jr. | |
| 7,334,594 B2 * | 2/2008 | Ludin | 137/1 |
| 7,394,182 B2 * | 7/2008 | Pelrine et al. | 310/328 |
| 7,621,886 B2 * | 11/2009 | Burnett | 604/9 |
| 2003/0214199 A1 * | 11/2003 | Heim et al. | 310/309 |

* cited by examiner

*Primary Examiner* — Tatyana Zalukaeva
*Assistant Examiner* — Philip R Wiest
(74) *Attorney, Agent, or Firm* — Gerald E. Hespos; Michael J Porco

(57) ABSTRACT

A cerebrospinal fluid (CSF) shunt comprises a ventricular catheter and an electroactive polymer actuated valve for regulating the drainage rate of CSF from the brain ventricle of a patient. The shunt system also comprises a distal catheter for discharge of the CSF to a separate location in the patient's body such as the peritoneal cavity or atrium of the heart. The electroactive polymer actuated valve regulates the flow rate of CSF through a predetermined threshold pressure, which can be adjusted and programmed externally from the patient's body by means of an external control unit signal, as well as through a signal indicated by an internal sensor or an electroactive polymer transducer. The sensor also communicates a signal to the external control unit for indicating the internal pressure at a single location or multiple locations throughout the fully implanted shunt assembly.

17 Claims, 6 Drawing Sheets

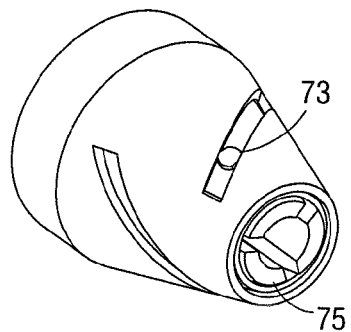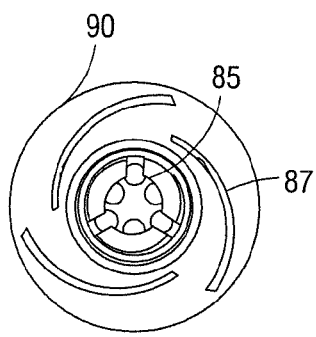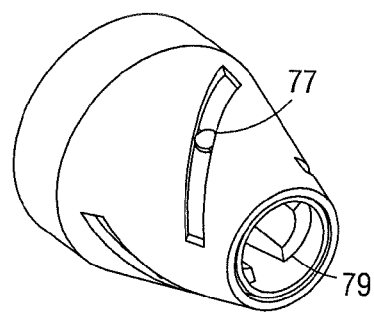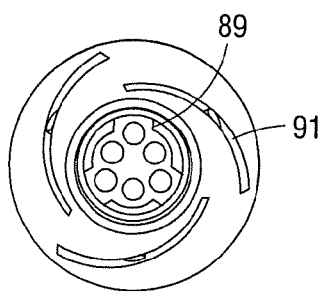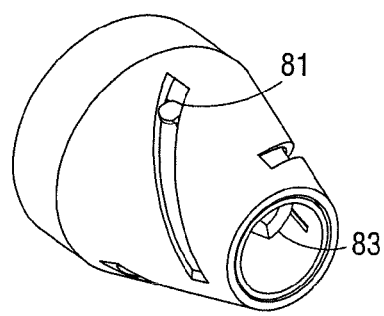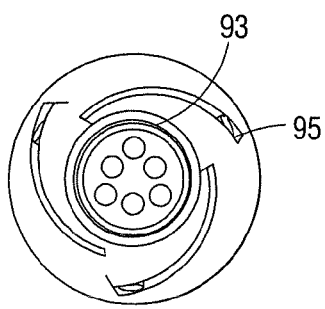
FIG. 4     FIG. 5

ELECTROACTIVE POLYMER ACTUATED CEREBROSPINAL FLUID SHUNT

CROSS-REFERENCE TO RELATED APPLICATIONS

This application claims the benefit of the filing date of provisional application No. 60/846,952, filed Sep. 24, 2006.

FIELD OF THE INVENTION

The present invention relates to shunt systems and methods for removing or draining cerebrospinal fluid from the brain ventricle of a patient to control intracranial pressure for the treatment of hydrocephalus and other diseases.

BACKGROUND OF THE INVENTION

Cerebrospinal fluid (CSF) is a clear bodily fluid that is primarily produced by the choroid plexus and continuously circulates throughout the ventricular system of the brain and around the spinal cord. The essential function of CSF is to provide a protective cushion to the brain and spinal cord in that it acts as a shock absorber by keeping the brain and spinal cord buoyant, which ultimately can prevent injuries to the central nervous system.

The abnormal accumulation of CSF in the brain ventricles consequently leads to the condition of hydrocephalus through the obstruction or excessive production of CSF in the brain. Hydrocephalus, as a result, is characterized by an elevated intracranial pressure (ICP) which ultimately causes pressure that can compress the brain tissue and dilate the ventricles. If left untreated, hydrocephalus can lead to other dangerous conditions, including subdural hematoma, impaired blood flow, coma, or even the eventual death of a patient. Thus, to effectively reduce elevated ICP, the drainage and rerouting of CSF to a secondary location within the body is an essential solution for patients with congenital or acquired hydrocephalus.

The removal and drainage of CSF has been achieved with varying levels of success in the past and present through the use of shunt systems. Shunt systems are typically made up of a ventricular catheter, which is inserted into the brain ventricle and connected to a valve that conducts the fluid away from the brain to be reintroduced into the peritoneal cavity or into the vascular system through a distal catheter to essentially maintain the proper pressure in the brain ventricles. Although many of the existing shunt systems have been implemented with successful results, they can still present problems given certain circumstances.

A primary example of an essential problem that has existed within the use of typical shunt systems is in the inability to adjust the threshold pressure within the shunt valve. Shunt systems typically allow fluid flow only when the fluid pressure reaches a threshold pressure for the shunt valve. However, due to the constantly changing physiological parameters of a patient over time, the threshold pressure must be adjusted. For example, an initial setting on the valve can be determined based upon the patient's preoperative ventricular CSF pressure, which could be most optimal at a relatively low threshold pressure. Once the shunt system has been implanted, the pressure may often need further adjustment to stabilize the ventricle size. This is essential because if the valve pressure is not adjusted, it could lead to the overdrainage of CSF from the brain ventricle or the accumulation of CSF within the ventricles resulting in an elevated ICP. As an alternative to surgically re-implanting the shunt system for adjustments after the initial threshold pressure has been defined, non-invasive methods have been in use to effectively achieve this.

The use of a programmable shunt system, which was first disclosed by Hakim in U.S. Pat. Nos. 4,615,691 and 4,772,257, has most significantly provided an efficient method for overcoming the difficulties discussed regarding the constant need for pressure adjustment of the shunt valve. The methods disclosed in these patents for an adjustable-pressure valve is commercially known as the Codman Hakim Programmable and Medtronic Strata valves. These particular shunts use an externally adjustable CSF shunt valve which has a variable pressure through the implementation of a magnetic field which is applied outside of the patient's body. The magnetic field ultimately actuates an internal stepper motor to vary the threshold pressure within the shunt valve. Although this has provided an important solution to some of the most essential problems associated with shunts, existing shunt systems in general still do not have the ability to adjust threshold pressures autonomously in accordance with the constantly changing physiological constraints of a patient which inevitably change over time.

The concept of using a sensor for detecting pressure changes which can provide an externally communicated signal along with a direct signal to the actuating element for autonomous valve pressure adjustment, is, however, a method for improving upon certain difficulties concerning fluid flow and pressure which has also been addressed in a number of different patents. These patents all discuss a variety of different methods, but there are also many limitations to the methods presented due to how the sensor and actuating elements effectively adjust the threshold pressure.

These limitations are often a result of the particular means for actuation, such as the constant reliability to an electromagnetic actuator. This particular form of actuation in itself has its own restrictions, especially with regard to how it can be used or coupled to a sensing element and how that sensing element directly functions with the actuating element with regard to shunt systems in general. By using a different kind of actuator then magnetic energy, i.e., one that can act as both an actuator and as a transducer through taking advantage of the deflection used to detect the pressure imposed upon it, a reduction in the number of mechanical components can also be an advantageous result in that it would provide a simplified assembly and fabrication method for the mechanical features of the shunt valve. The implementation of existing magnetically actuated shunt valves also do not provide a means for a sensing element that is directly coupled to the means for actuation, which can also be improved upon through the use of alternative actuation methods.

Accordingly, an implantable shunt system which is capable of adjusting its threshold valve pressure through the use of alternative methods for an actuator and the mechanical properties by which that actuator functions with, along with an alternative means for sensing, can provide a number of advantages over previously existing shunt systems. The problems that can be improved upon concern not only the ability to have an automatically adjustable pressure valve, which is also externally programmable, but also including the detection of pressures that exist within the implanted shunt assembly which can be communicated to an external point outside of the patient's body.

SUMMARY OF THE INVENTION

The present invention provides an implantable shunt system that utilizes an electroactive polymer actuated valve for the control and regulation of cerebrospinal fluid (CSF) being redirected from the brain ventricle to a secondary cavity within the body such as the peritoneal cavity or atrium of the heart. The electroactive polymer actuated valve also includes a ventricular catheter coupled to the inlet aperture of the valve and a distal catheter coupled to the outlet aperture of the valve.

It is an object of this invention to utilize an electroactive polymer as not only an actuating element for the adjustable threshold pressure and control of CSF, but also as a transducer for sensing pressure which is imposed upon or within the shunt system from the pressure created by the CSF. This can be achieved due to the utilization of an electroactive polymer's energy conversion properties, in that it can convert mechanical energy into electrical energy as well as having the ability to convert electrical energy into mechanical energy. This can be achieved in different ways depending on the configuration and location of the electroactive polymer transducer within the full shunt assembly.

In one embodiment, the differential pressure between the ventricular catheter and the distal catheter results in the deflection of the electroactive transducer which can provide a voltage to be used as a means for communicating a signal to either the actuating portion of the same electroactive polymer or a secondary electroactive polymer, utilized specifically for actuation of the valve. This can, as a result, provide both actuation and responsive adjustment to the pressure required for the valve within the shunt system.

In another embodiment the embodiment, the mechanical properties of the valve are arranged such that a reduction in the number of mechanical components, which would typically be needed for a programmable magnetically actuated shunt, are not necessary for the same results. In this same embodiment, the electroactive polymer is coupled to a spring within a ball and spring valve assembly. The advantage to this configuration is in the fact that when the electroactive polymer is provided an electrical voltage, it will deflect and move along a fixed level guide that does not require any movement. Once the actuator is fixed to a different level, the force acting upon the ball from the coupled spring element will ultimately increase or decrease the force on the ball, which in turn varies the overall valve pressure.

In another preferred configuration the electroactive polymer is coupled to a plurality of mechanical components which can assist in both the actuation of the spring against the ball set in the aperture, within a ball and spring valve configuration, as well as in the detection of the differential pressure between the ventricular catheter and the distal catheter. The use of these additional mechanical components also can provide a method for the decrease in the possibility of potential obstruction in the shunt valve. Although obstruction or clogging most frequently occurs at the ventricular end of the shunt system, it may also occur at any point along the shunt system including the valve.

Additionally, the electroactive polymer actuated valve can be regulated by an external control unit which has an embedded transceiver which can receive the signals given off by the transducer portion of the electroactive polymer, indicating pressure changes, or transmit signals to a secondary control unit which will ultimately indicate actuation for the pressure adjustment of the shunt valve.

These features and advantages of the present invention will be further described in accordance with the following description and associated figures.

BRIEF DESCRIPTION OF THE DRAWINGS

FIG. 4 shows another embodiment of a shunt valve showing a series of isometric views which utilizes the means of rotational electroactive polymer actuation.

FIG. 5 is a side elevation view of the same sequence illustrated in FIG. 4.

DETAILED DESCRIPTION OF THE INVENTION

Figure 1:
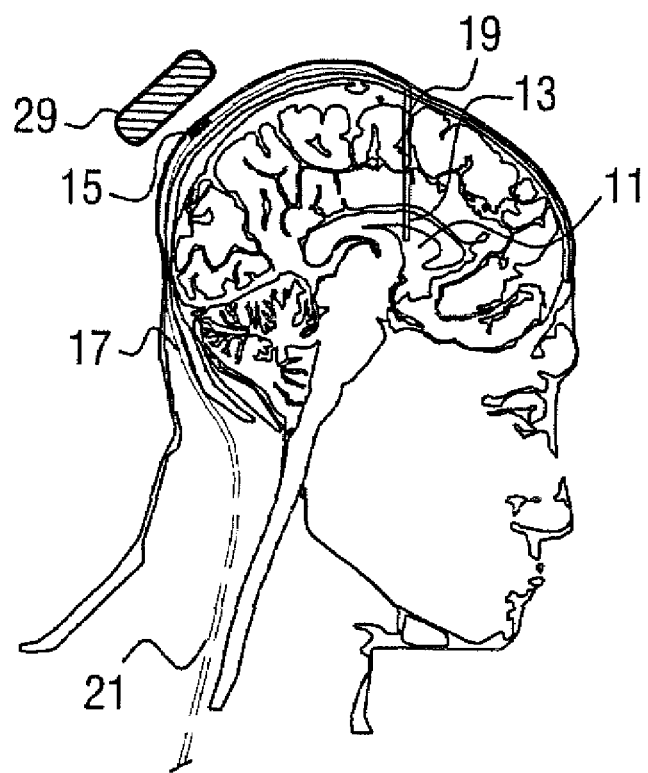
FIG. 1 is a diagram showing the side view of a patient with the implanted CSF shunt system along with the external control unit.
Figure 1:
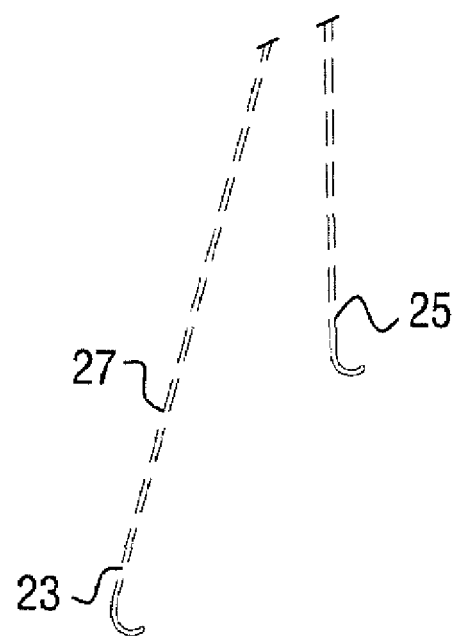

In the embodiment present in FIG. 1, a typical cerebrospinal fluid (CSF) shunt is shown with all of its essential elements and how they are implanted within a patient's body. The electroactive polymer actuated shunt valve 15 is located at a point underneath the scalp of a patient which is coupled to a ventricular catheter 19 that is inserted into the brain ventricle 11. The ventricular catheter 19 receives CSF from its distal end 13 which flows to the electroactive polymer actuated shunt valve 15. The control and regulation of the flow of CSF is ultimately defined by a predetermined threshold pressure which can ultimately be adjusted through the external control unit 29, which is placed directly over the scalp protrusion where the shunt valve 15 is located. Once the threshold pressure is defined and/or continuously adjusted based upon pressure levels read by an electroactive polymer transducer, or a sensor also coupled to the shunt valve 15, the valve redirects the CSF to a distal catheter 17. The drainage of CSF is ultimately discharged through a distal catheter 21 which is coupled to the outlet aperture of the shunt valve 15. The drainage can occur at two separate locations which include the peritoneal cavity, where a distal catheter 27 and its relative outlet opening 23 is located to provide CSF drainage, or through an alternative method utilizing an atrium located distal catheter 25, which redirects CSF to the atrium of the heart.

Figure 2:
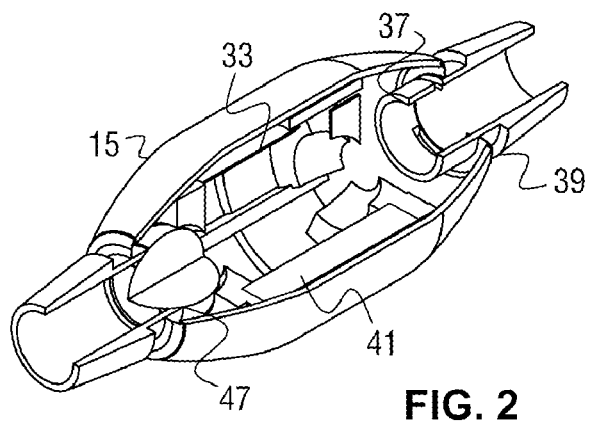
FIG. 2 shows a sectional isometric view of the implantable shunt valve in accordance with one embodiment using electroactive polymer actuators coupled to mechanical components.
Figure 3:
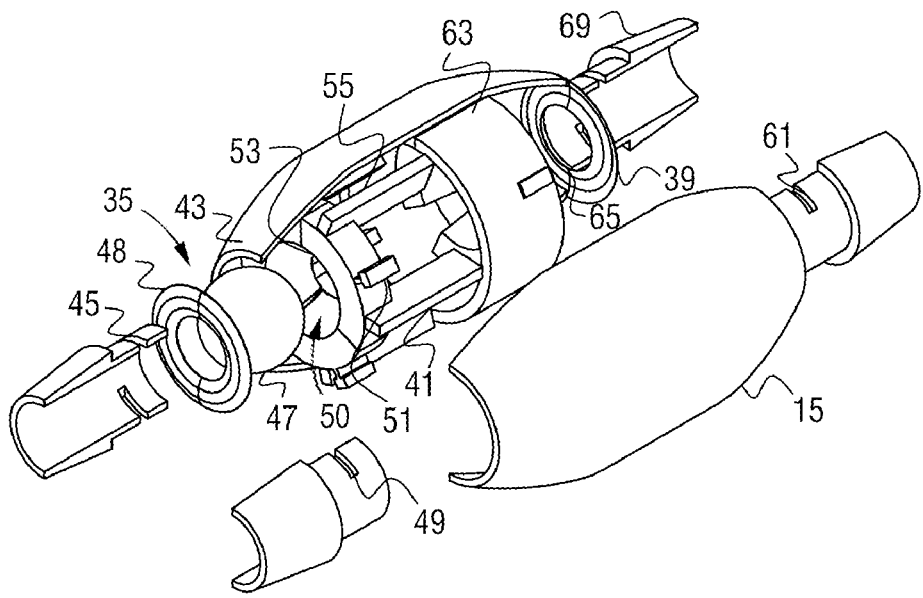
FIG. 3 shows an exploded isometric view of the same embodiment of the shunt valve illustrated in FIG. 1.

The shunt valve 15 shown in FIG. 2, as one preferred embodiment, has a ball and spring valve 35 situated at the inlet aperture 45 and 49 which can also be seen in FIG. 3 as well. The CSF ultimately flows through the primary valve chamber 33, but is first controlled and brought through the inlet aperture 45 and 49, which can initially provide a filtering effect due to smaller openings located within the inlet aperture 45 and 49 to assist in the prevention of potential obstruction which can be caused by debris, bacteria, or coagulated blood. These smaller openings, or slits, located within inlet aperture 45 and 49, can also provide an immediate shut off feature of any fluid before entering the ball and spring valve opening 50. This immediate shut off feature can be achieved by the motion of the electroactive polymer actuated sliding elements 55 and 41. These electroactive polymer actuated sliding ring elements 53 also provide a number of other features to the shunt valve 15. It is important to note that although there are a plurality of electroactive polymers present within these drawings and descriptions, the electroactive polymer discussed in accordance with the invention can be implemented as a single electroactive polymer opposed to a multiple set of them. The electroactive polymers 55 and 41 should be hermetically sealed such that it prevents any interference with the fluid passing through the full valve assembly 15.

Electroactive polymers, also known as "conducting electroactive polymers," can be used for both actuation and sensing which ultimately presents one of the essential elements to provide particular advantages to this disclosed invention. Electroactive polymers are unique in that they can convert mechanical energy into electrical energy and electrical energy into mechanical energy. This can be achieved when the electroactive polymer acts as an insulated dielectric between two electrodes, whereby the polymer deflects when receiving a voltage difference between both electrodes. A variety of electroactive polymers can be implemented with varying degrees of optimization. Sulfonated Polyaniline, for example, is an electroactive polymer which has one of the more efficient conducting capacities and could be optimal for different uses. Other electroactive polymers that exist include polypyrrole, polyacetylene and polythiophene, along with polyaniline as well.

Accordingly, the shunt valve 15 implements the use of electroactive polymers 55 and 41 to actuate the sliding ring elements 53 which provides a force on the ball 47 through a spring 48 directly attached to the smaller opening at the back of the sliding ring elements 53, thus providing a fixed threshold pressure when the guiding post element 51 is variably fixed within a secondary guiding element hub 63. The guiding element hub 63 is shown at one end of the valve in FIG. 3, but it is also located at where the sliding ring elements 53 and their respective guiding post elements 51 are directly engaged with each other for proper mechanical support and function.

The electroactive polymers 55 and 41 can ultimately be actuated to change the pressure of the shunt valve in addition to other features directly through a signal received from different sources. The first source is ultimately through the detection of a pressure differential within the same shunt valve 15, whereby the electroactive polymers 55 and 41 can take a force from both sides of the valve, due to the fact that they are positioned to run throughout the full length of the valve 15, to ultimately read the differential pressure between the distal catheter connected to the outlet aperture 65 and the ventricular catheter pressure connected to the inlet aperture 43. It is essential to emphasize that the electroactive polymers 55 and 41 are being utilized as a transducer in this instance, providing the ability to transfer this mechanical energy to an electric voltage because of the resulting deflection of the electroactive polymers 55 and 41. This electrical voltage can in turn provide not only a means for translating a signal back to the actuator, but it can also act as a form of energy to provide the continuing adjustment of the valve's threshold pressure. The voltage created by this deflection can also be transmitted to an external control unit outside of the body as seen in FIG. 1.

The embodiment presented in FIGS. 2 and 3 provide advantages due largely in part to the fact that they are operatively engaged with additional mechanical components. In another embodiment, to be discussed in further detail, similar features are provided but without the reliability to additional mechanical components.

In the embodiment shown in FIGS. 4 and 5, the utilization of a similar method to provide a threshold pressure from a shunt valve aperture is provided, but instead through the means of rotational actuation by the implementation of an electroactive polymer. The drawings are shown in this instance to emphasize the use of a rotational valve system, whereby the guiding notch 73, 77 and 81 is directly translating a rotational movement to a linear movement for sliding elements 75, 79 and 83. The holes 85 located at the back of the valve aperture 90, can additionally provide an alternative fluid flow or another means for filtering any potential obstructive elements.

Figure 6:
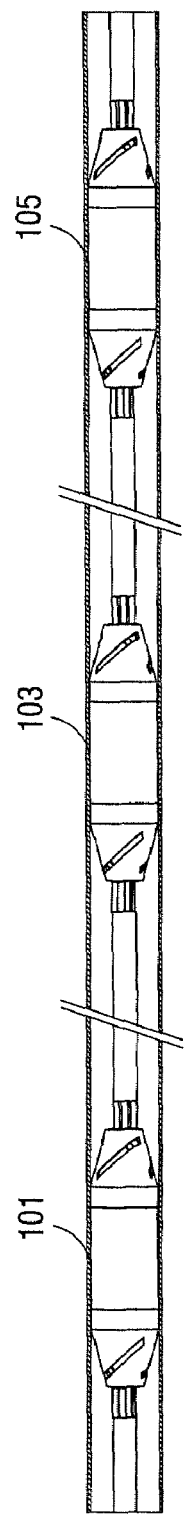
FIG. 6 shows a catheter configuration utilizing multiple control valves.
Figure 7:
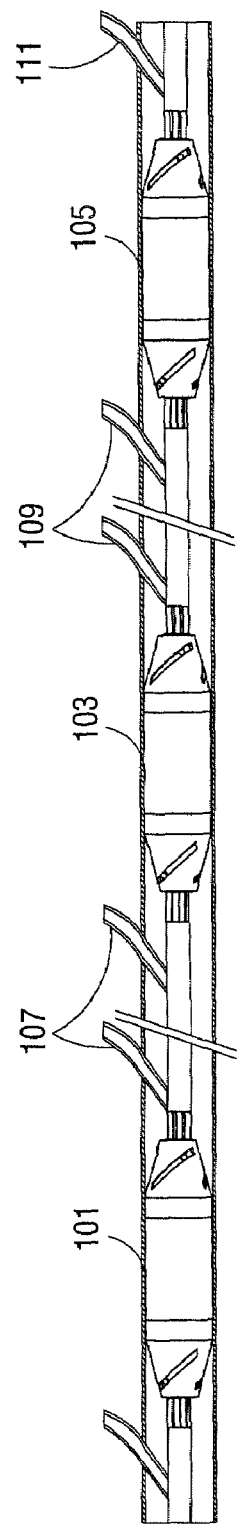
FIG. 7 shows a catheter configuration utilizing multiple control valves which also include extension tubes as an additional means for pressure sensing.

The use of still another means for fluid control in shown in FIGS. 6 and 7 where multiple control valves 101, 103 and 105 are placed throughout the catheter. This configuration could be beneficial when more than one catheter is operating and inserted into the ventricular systems in that it would provide for additional outlet ports 107, 109 and 111 for either further drainage or for coupling those catheters to an additional system.

Figure 8:
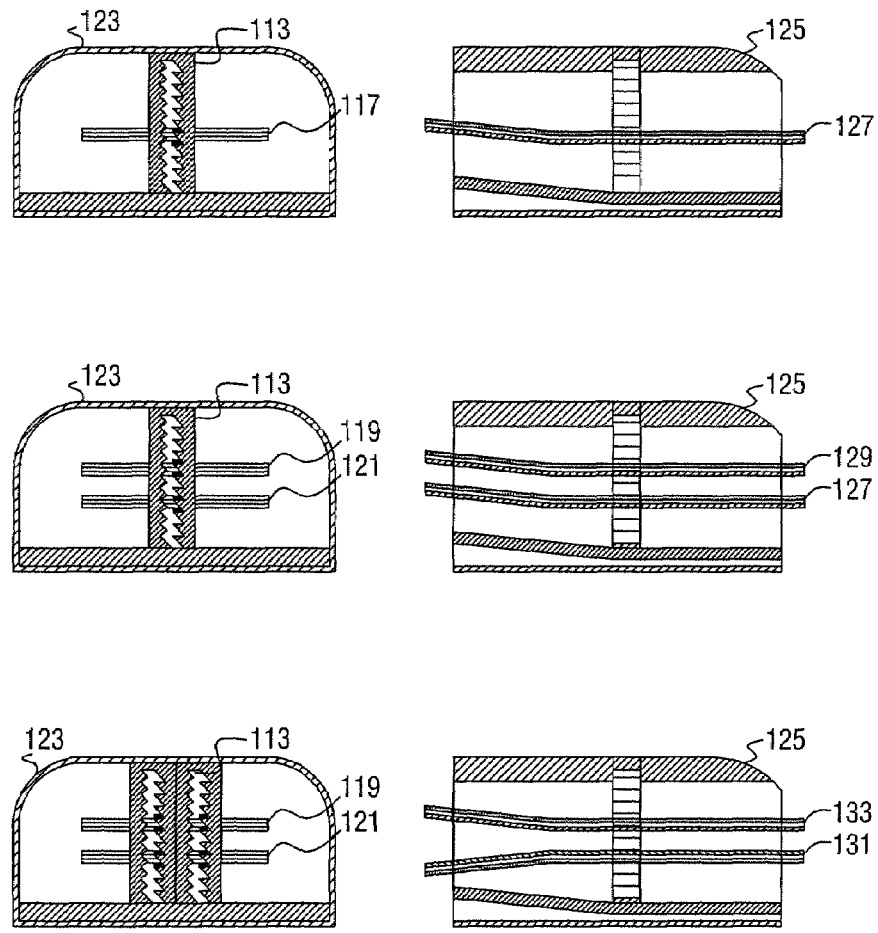
FIG. 8 illustrates two sets of sectional views which correspond to another embodiment that utilizes an electroactive polymer which is coupled to a spring and a transducer for a ball and spring valve assembly.

A simplified method for a shunt system is provided in FIG. 8. Although it uses similar methods from previously disclosed embodiments of the invention and also existing shunt systems in general, this method, however, uses fewer mechanical components. The shunt valve shell 123 and 125, has a single linearly fixed guide 113, which ultimately supports an electroactive polymer which is coupled to a spring to be implemented with a ball and spring valve aperture. The linearly fixed guide 113 has embedded slots for the electroactive polymer to rest upon when the threshold pressure and flow control is set to a different level. The electroactive polymer 119 and 121 can either ascend or descend along the linearly fixed guide 113. As a result of this configuration, the electroactive polymers will not only have the ability to read differential pressures as mentioned with methods previously discussed, but it can reduce the amount of moving mechanical components, while actuating the adjustment in the threshold pressure within the shunt valve as well.

Figure 9:
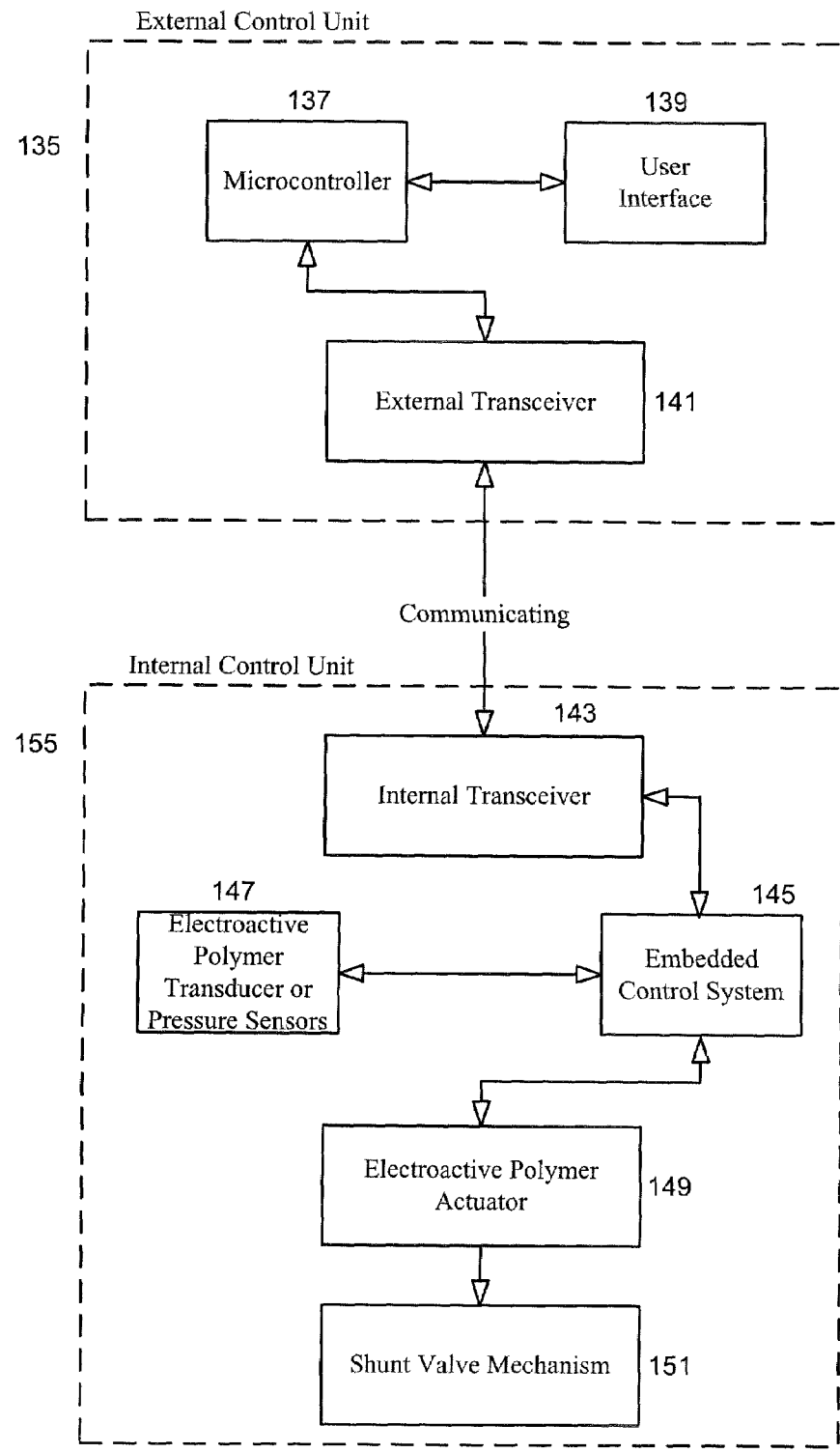
FIG. 9 is flow diagram of a typical device control configuration including an external control unit and an internal control unit.

FIG. 9 shows a flow diagram of a typical device control configuration including an external control unit and an internal control unit. Within the internal control unit 155, the pressure changes can be detected by a pressure sensor or by an electroactive polymer transducer which is also housed with the embedded control system 145 which can provide a communicating signal from an internal transceiver 143. This signal is in turn transmitted to an external transceiver 141, a microcontroller 137, and user interface 139, all housed within an external control unit to ultimately provide information to a surgeon for further evaluation of how the shunt system is essentially operating, and whether or not adjustment is needed. The internal pressure changes can ultimately be detected and signaled back to the electroactive polymer actuator 151 to ultimately control the fluid regulation and flow, along with the determination of the effective threshold pressure.

There are many variations and alternatives to the embodiments of the disclosed invention including references to specific details. However, these variations and details should not be limiting to the entirety of the invention, except as and to the extent that they are included in the accompanying claims.

What is claimed is:
1. A cerebrospinal fluid shunt system comprising:
a valve having a longitudinal axis, the valve comprising an electroactive polymer, a ring element, a ball, and a spring, the spring positioned between the ring element and the ball, wherein, when actuated, the electroactive polymer is configured to apply a force to the ring element in a longitudinal direction parallel to the longitu- dinal axis causing the ring element to slide in the longitudinal direction and thereby provide a force on the ball through the spring;

the electroactive polymer being configured as a pressure sensor to detect a pressure differential between an inlet of the valve and an outlet of the valve;

an internal control unit configured to transmit the detected pressure differential; and an external control unit configured to receive the transmitted pressure differential;

wherein, in response to receiving the pressure differential, the external control unit provides a signal to the electroactive polymer causing the electroactive polymer to modify a force on the ring element to adjust the valve pressure, thereby allowing the valve pressure to be adjusted after the valve has been implanted in a patient.

2. The cerebrospinal fluid shunt system as in claim 1, wherein the electroactive polymer senses pressure created by cerebrospinal fluid, wherein the sensed pressure is used to adjust the valve pressure.

3. The cerebrospinal fluid shunt system as in claim 1, wherein the electroactive polymer is further configured to apply the force to the ring element in a direction with or against the flow of the cerebrospinal fluid through the valve.

4. A shunt system implantable in a body comprising:
a ventricular catheter having a first end and a second end, the first end of the ventricular catheter configured to be inserted into the brain ventricle within the body;
a distal catheter having a first end and a second end, the first end of the distal catheter configured to be inserted into a secondary cavity within the body; and
an electroactive polymer actuated valve having a longitudinal axis and comprising an inlet aperture and an outlet aperture, the second end of the ventricular catheter coupled to the inlet aperture and the second end of the distal catheter coupled to the outlet aperture, the electroactive polymer actuated valve configured to regulate a flow rate of cerebrospinal fluid (CSF) being redirected from the brain ventricle to the secondary cavity, the electroactive polymer actuated valve having an adjustable threshold pressure to regulate the flow rate of the CSF;
wherein the flow rate of the CSF is adjusted by actuating at least one electroactive polymer of the electroactive polymer actuated valve to cause the at least one electroactive polymer to apply a force, directed in a longitudinal direction parallel to the longitudinal axis, to a moveable ring element within the electroactive polymer actuated valve causing the moveable ring element to slide in the longitudinal direction and thereby modify a force on a ball within the electroactive polymer actuated valve, thereby allowing the CSF to be adjusted after the shunt system has been implanted in the body, the electroactive polymer actuated valve having a spring member disposed between the moveable ring element and the ball.

5. The implantable shunt system as in claim 4, further comprising an external control unit for adjusting the threshold pressure externally from the body.

6. The implantable shunt system as in claim 4, wherein the at least one electroactive polymer is configured as a transducer for sensing pressure created by the CSF, wherein the sensed pressure is used to adjust the threshold pressure.

7. The implantable shunt system as in claim 6, wherein a differential pressure between the ventricular catheter and the distal catheter results in a deflection of the at least one electroactive polymer which converts mechanical energy of the deflection into a voltage signal for actuating the electroactive polymer actuated valve.

8. The implantable shunt system as in claim 7, wherein the voltage signal created by the deflection is transmitted to an external control unit outside of the body.

9. The implantable shunt system as in claim 4, wherein:
the spring member is disposed between the ring element and the ball at the inlet aperture, wherein the ring element, ball, and spring member are configured to control the flow rate through the electroactive polymer actuated valve;
wherein the at least one electroactive polymer is disposed in a primary valve chamber of the electroactive polymer actuated valve and is configured for actuating the ring element, ball, and spring member.

10. The implantable shunt system as in claim 9, wherein the inlet aperture includes at least one opening to provide a filtering effect.

11. The implantable shunt system as in claim 4, wherein actuating the at least one electroactive polymer causes the at least one electroactive polymer to apply the force to the moveable ring element in a direction with or against the flow of the CSF through the electroactive polymer actuated valve.

12. A shunt system implantable in a body comprising:
an electroactive polymer actuated means for regulating a flow rate of cerebrospinal fluid (CSF) being redirected from the brain ventricle to a secondary cavity within the body, the electroactive polymer actuated means having an adjustable threshold pressure to regulate the flow rate of the CSF, the electroactive polymer actuated means configured to regulate the flow rate by applying a force to a moveable ring element in a longitudinal direction parallel to a longitudinal axis of the electroactive polymer actuated means, the force causing the moveable ring element to slide in the longitudinal direction and thereby modify a corresponding force on a ball through a spring positioned between the ring element and the ball, wherein the moveable ring element, ball, and spring reside within a flow path of the CSF;
means for sensing pressure created by the CSF and generating a signal indicative of the pressure; and
control means for receiving the pressure signal and controlling the electroactive polymer actuated means, based on the sensed pressure, to regulate the flow rate of the CSF after the shunt system is implanted in the body.

13. The implantable shunt system as in claim 12, further comprising an external control means for adjusting the threshold pressure externally from the body.

14. The implantable shunt system as in claim 12, wherein the means for sensing creates a signal readable externally from the body.

15. The implantable shunt system as in claim 12, further comprising a means for filtering the CSF flowing through the electroactive polymer actuated means.

16. The implantable shunt system as in claim 12, further comprises a catheter having one end disposed in the brain ventricle and a second end disposed in the secondary cavity within the body and at least two electroactive polymer actuated means.

17. The implantable shunt system as in claim 12, wherein the electroactive polymer actuated means is configured to apply the force to the moveable ring element substantially parallel with the flow path of the CSF at the electroactive polymer actuated means.

* * * * *